US009919015B2

(12) United States Patent
Turner et al.

(10) Patent No.: US 9,919,015 B2
(45) Date of Patent: Mar. 20, 2018

(54) COMPOSITION AND METHOD FOR INHIBITING HERPESVIRIDAE INFECTIONS

(71) Applicant: VIRATEC PTY LTD, South Australia (AU)

(72) Inventors: Ross Walter Turner, Kensington Park (AU); Jonathan Tversky, South Yarra (AU)

(73) Assignee: VIRATEC PTY LTD, South Australia (AU)

( * ) Notice: Subject to any disclaimer, the term of this patent is extended or adjusted under 35 U.S.C. 154(b) by 152 days.

(21) Appl. No.: 14/532,769

(22) Filed: Nov. 4, 2014

(65) Prior Publication Data

US 2015/0056313 A1    Feb. 26, 2015
US 2017/0368125 A9    Dec. 28, 2017

Related U.S. Application Data

(62) Division of application No. 12/067,831, filed as application No. PCT/AU2006/001382 on Sep. 22, 2006, now abandoned.

(30) Foreign Application Priority Data

Sep. 23, 2005 (AU) .................................. 2005905245

(51) Int. Cl.
    *A61K 36/287*    (2006.01)
    *A61K 47/10*     (2017.01)
    *A61K 47/06*     (2006.01)
    *A61K 9/00*      (2006.01)
    *A61K 9/06*      (2006.01)

(52) U.S. Cl.
    CPC ............ *A61K 36/287* (2013.01); *A61K 9/006* (2013.01); *A61K 9/0014* (2013.01); *A61K 9/0034* (2013.01); *A61K 9/0043* (2013.01); *A61K 9/06* (2013.01); *A61K 47/06* (2013.01); *A61K 47/10* (2013.01)

(58) Field of Classification Search
None
See application file for complete search history.

(56) References Cited

U.S. PATENT DOCUMENTS

| 4,675,313 A | 6/1987 | Arias |
| 5,834,000 A | 11/1998 | Yng-Wong |
| 2002/0182272 A1 | 12/2002 | Halstead |

FOREIGN PATENT DOCUMENTS

| CN | 1391931 A | 1/2003 |
| CN | 1589820 A | 3/2005 |
| JP | 2005035899 A | 2/2005 |
| WO | WO 2007033419 A1 * | 3/2007 ........... A61K 9/0014 |

OTHER PUBLICATIONS

"Asteraceae (Compositae)". Retrieved from the Internet on: Jul. 5, 2016 [Retrieved from: URL: <http://www.botany.hawaii.edu/faculty/carr/aster.htm>].*
"Chrysanthemum". The Plant List (2010). Version 1. Published on the Internet; http://www.theplantlist.org/ (accessed Jan. 1).*
McIntyre, A. "Herpes" from Herbs for Common Ailments (1992). pp. 33 and 74.*
Liu, W. "A safe and effective approach to genital herpes". Internet archive date: Jul. 1, 2004 [Retrieved from the Internet on Apr. 30, 2014]. Retrieved from the Internet: <URL: https://web.archive.org/web/20040701035704/http://www.tcmpage.com/hpgenitalherp.html.>.
CDC:STD Prevention—Genital Herpes. Internet Archive Date: Jun. 3, 2004 [Retrieved from the Internet on: Oct. 6, 2011]. Retrieved from the Internet: <URL: http://web.archive.org/web/20040603021732/http://www.cdc.govistd/ Herpes/STDFact-Herpes.htm>.
Akihisa et al., "Triterpene Alcohols from the Flowers of Compositae and Their Anti-Inflammatory Effects," Phytochem. 43(6):1255-60(1996).
Ukiya et al.,"Constituents of Compositae Plants III. Anti-tumor Promoting Effects and Cytotoxic Activity Against Human Cancer Cell Lines of Triterpene Diols and Triols from Edible Chrysanthemum Flowers," Cancer Lett. 177:7-12 (2002).
International Search Report for PCT/AU2006/001382 (dated Nov. 3, 2006).

* cited by examiner

*Primary Examiner* — Amy L Clark
(74) *Attorney, Agent, or Firm* — Bond, Schoeneck & King, PLLC; Joseph Noto

(57) ABSTRACT

The present invention relates to a pharmaceutical composition when used for inhibiting a herpesviridae infection and/or providing relief from a herpesviridae infection in a subject. The composition includes an effective amount of an extract from a plant in the Asteraceae family.

5 Claims, No Drawings

COMPOSITION AND METHOD FOR INHIBITING HERPESVIRIDAE INFECTIONS

This application is divisional of U.S. patent application Ser. No. 12/067,831, filed Aug. 12, 2008, which is a U.S. national stage entry of International Patent Application Number PCT/AU2006/001382, filed Sep. 22, 2006, which claims priority from Australian Provisional Patent Application No. 2005905245 filed on 23 Sep. 2005.

FIELD OF THE INVENTION

The present invention relates to a composition and method for inhibiting herpesviridae infections.

BACKGROUND OF THE INVENTION

For many viruses, the prevalence of infection in the general population is very high. Viruses of the herpesviridae family, such as herpes simplex virus, varicella zoster virus and Epstein Barr virus, are all viruses that infect a large proportion of the population on a regular basis. In some cases, the majority of the population will be infected during their lifetime.

For example, in the case of herpes simplex virus type 1 (HSV-1), the virus infects 40 to 60% of teenagers and young adults, and over 90% of the population by 60 years of age. This virus commonly infects the circumoral regions, both inside and outside the mouth. The natural course of the illness ranges from 10 days to 4 weeks, dependent on the extent of infection and the host status. Common clinical manifestations of HSV-1 infection are primary herpetic stomatitis and recurrent herpes labialis.

Herpes simplex type 2 (HSV-2) is the commonest causal agent for herpetic genital infections. It is estimated that 10% of the population in Western countries have genital herpes, but that only 20 to 25% of infected individuals are aware of their condition.

Herpes Zoster is a recurrent infection of the varicella-zoster virus (chickenpox virus) and has an incidence of 0.4 to 1.6 cases per 1000 among healthy people less than 20 years of age, rising to an incidence of 4.1-11.0 per 1000 for people greater than 80 years of age. The virus causes a wide range of problems affecting the skin and the eye. After the initial infection (chicken pox), the virus lays dormant in nerve cells and then becomes reactivated as a result of many factors such as aging, stress, suppression of the immune system, and certain medications.

Oral hairy leukoplakia (OHL) is an oral mucosal disease. It is due to infection by Epstein-Barr virus (EBV) and occurs most commonly in subjects who are immunocompromised, particularly those infected with HIV.

For most of these viruses, there is no effective treatment once infection has occurred. Oral and/or topical antivirals such as acyclovir, famciclovir and valcicovir are often prescribed with herpes simplex and herpes zoster infections, or for the treatment of oral hairy leukoplakia. However, the efficacy of such agents is often limited. In addition, such agents often require an extended treatment regime and the timing of commencement of treatment can determine its efficacy. For example, in the case of HSV-1 and HSV-2 lesions, it is recommended that treatment is started within 1 hour of prodrome, while for Herpes Zoster, treatment should be started within 72 hours of signs of rash.

The current treatment of herpesviridae infections is inadequate for many reasons. Accordingly, there is a need for new compositions and methods that have the capacity to inhibit such infections.

The present invention relates to the use of extracts from plants in the Asteraceae family to inhibit infection by viruses in the herpesviridae family, and the use of the extracts to provide relief from such infections.

A reference herein to a patent document or other matter which is given as prior art is not to be taken as an admission that that document or matter was known or that the information it contains was part of the common general knowledge as at the priority date of any of the claims.

SUMMARY OF THE INVENTION

The present invention provides a pharmaceutical composition when used for inhibiting a herpesviridae infection and/or providing relief from a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides use of an effective amount of an extract from a plant in the Asteraceae family in the preparation of a medicament for inhibiting a herpesviridae infection and/or providing relief from a herpesviridae infection in a subject, wherein the extract is not an extract from a plant in the sub-families Heliantheae and Asteroideae, or an extract from a plant in the genus *Youngia*.

The present invention also provides a method of inhibiting a herpesviridae infection and/or providing relief from a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

The present invention also provides a pharmaceutical composition when used for one or more of preventing, treating and providing relief from a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides a method of preventing, treating and/or providing relief of a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

The present invention also provides use of an effective amount of an extract from a plant in the Asteraceae family in the preparation of a medicament for one or more of preventing, treating and providing relief from a herpesviridae infection in a subject, wherein the extract is not an extract from a plant in the sub-families Heliantheae and Asteroideae, or an extract from a plant in the genus *Youngia*.

The present invention also provides a pharmaceutical composition when used for one or more of preventing, treating and providing relief of a disease or condition associated with a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides a method of preventing, treating and/or providing relief of a disease or condition associated with a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

The present invention also provides use of an effective amount of an extract from a plant in the Asteraceae family in the preparation of a medicament for one or more of preventing, treating and providing relief of a disease or condition associated with a herpesviridae infection in a subject, wherein the extract is not an extract from a plant in the sub-families Heliantheae and Asteroideae, or an extract from a plant in the genus *Youngia*.

The present invention also provides a pharmaceutical composition when used for one or more of preventing, treating and providing relief from a disease or condition selected from chicken pox, shingles, herpetic oral ulceration, conjunctivitis, genital herpes, gingivostomatitis, herpes labialis, neonatal herpes, keratoconjunctivitis, aseptic meninginitis, mononucleosis, oral hairy leukoplakia, mononucleosis-like syndrome, pharyngitis, and viral pneumonia, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides a method of preventing, treating and/or providing relief of a disease or condition from a disease or condition selected from chicken pox, shingles, herpetic oral ulceration, conjunctivitis, genital herpes, gingivostomatitis, herpes labialis, neonatal herpes, keratoconjunctivitis, aseptic meningitis, mononucleosis, oral hairy leukoplakia, mononucleosis-like syndrome, pharyngitis, and viral pneumonia, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides use of an effective amount of an extract from a plant in the Asteraceae family in the preparation of a medicament for one or more of preventing, treating and providing relief of a disease or condition selected from chicken pox, shingles, herpetic oral ulceration, conjunctivitis, genital herpes, gingivostomatitis, herpes labialis, neonatal herpes, keratoconjunctivitis, aseptic meningitis, mononucleosis, oral hairy leukoplakia, mononucleosis-like syndrome, pharyngitis, and viral pneumonia, wherein the extract is not an extract from a plant in the sub-families Heliantheae and Asteroideae, or an extract from a plant in the genus *Youngia*.

The present invention also provides a method of producing a composition for inhibiting a herpesviridae infection in a subject and/or providing relief from a herpesviridae infection in a subject, the method including extracting all or part of a plant in the Asteraceae family with a substantially aqueous solvent, wherein the plant is not a plant in the sub-families Heliantheae and Asteroideae, or a plant from the genus *Youngia*.

The present invention arises out of studies into the treatment of herpesviridae infections with a botanical product derived from a plant in the daisy family. In particular, it has been found that an extract from the daisy *Chrysanthemum frutescens* has the capacity to inhibit herpesviridae infections in human subjects. The timing of commencement of treatment with the extract in human subjects does not appear to be as important as for some other anti-viral agents used to treat herpesviridae infections.

Various terms that will be used throughout the specification have meanings that will be well understood by a skilled addressee. However, for ease of reference, some of these terms will now be defined.

The term "extract" as used throughout the specification is to be understood to mean any fraction, preparation, purified or semi purified component, or concentrate derived from a plant in the Asteraceae family that is capable of inhibiting a herpesviridae infection. For example, the extract may be a complex mixture of plant constituents (e.g. as produced by maceration of all or part of a plant in a solvent such as water), or a fraction resulting from the concentration, purification or partitioning of one or more active ingredients present in the complex mixture.

In this regard, the extract will generally be combined with one or more pharmaceutically acceptable additives for use. However, it will be understood that under some circumstances the extract may also used alone to inhibit a herpesviridae infection.

The term "infection" as used throughout the specification is to be understood to mean any one or more of the steps involved after exposure of a subject to a virus of the family herpesviridae, including entry of virus into one or more of the cells in the subject, the replication of virus in one or more of the cells in the subject, the insertion of a viral genome into the host genome of one or more cells in the subject, or the lysis or extrusion of virus from one or more cells in the subject, or the subsequent effect of infection on the host.

In this regard, the phrase "a disease or condition associated with herpesviridae infection" is to be understood to mean a disease or condition in a subject caused by, and/or associated with, a herpesviridae infection in a subject.

The term "anti-viral agent" as used throughout the specification is to be understood to mean any agent that has the capacity to inhibit a herpesviridae infection.

The term "analgesia" (or variants thereof) as used throughout the specification is to be understood to mean the alleviation of pain and/or pain-related symptoms, including burning, stinging, tingling, soreness, itching, tenderness, discomfort, irritation and an inflamed and/or "drawing sensation". It will be further understood that the term "analgesia" means the alleviation of pain and/or pain-related symptoms without a significant anaesthetic or numbing effect.

GENERAL DESCRIPTION OF THE INVENTION

As mentioned above, in one embodiment the present invention provides a pharmaceutical composition used for inhibiting a herpesviridae infection and/or providing relief from a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

In this embodiment, the present invention provides a pharmaceutical composition including an extract from all or part of a plant in the Asteraceae family, wherein the composition inhibits herpesviridae infection in a subject.

The subject in the various embodiments of the present invention is a human or a suitable animal subject.

In addition to the anti-herpesviridae properties of the extract, the extract also has properties that ameliorate pain, discomfort and other undesirable sensations associated with the viral infection. For example, one property of the composition is an analgesic effect. This analgesic property is not due to a numbing principle associated with the composition.

Thus, the present invention may also be used for the relief of herpesviridae infections. In this regard, the term "relief" will be understood to include an amelioration of pain, discomfort or any other type of undesired sensation associated with the herpesviridae infection.

In one embodiment, the extract is produced from one of the following daisies: *Chrysanthemum* spp., including *Chrysanthemum frutescens*, varieties referred to as "Marguerite daisy", Ox-eye daisy (*Chrysanthemum leucanthemum*), *Chrysanthemum×morifolium, Chrysanthemum parthenium, Chrysanthemum vulgare, Chrysanthemum anethifolium, Chrysanthemum indicum*, and *Chrysanthemum balsamita; Olearia* spp., including *Olearia phlogopappa Olearia microphylla, Olearia ramulosa; Brachycome* spp., including *Brachycome multida* and *Brachycome iberidfolia; Arctotis* hybrids; *Celmisa* spp. including *Celmisa incana; Dimorphotheca* spp. including *Dimorphotheca aurantiaca*; and a daisy referred to as white oxyeye, white daisy, paris daisy, dog daisy, goldens, moon-daisy, maudlin daisy, field daisy, dun daisy, butter daisy, horse daisy, China aster, *bellis perennis, Leucanthemum vulgare*, or *Argyranthemum frutescens*.

In one embodiment, the extract is produced from all or part of a *Chrysanthemum frutescens* plant.

Examples of viruses of the herpesviridae family of virus include viruses of the alphaherpesvirinae, betaherpesvirinae and gammaherpesvirinae sub-families. Examples of viruses of the alphaherpesvirinae sub-family include herpes simplex virus type 1 and 2, and varicella-zoster virus. Examples of viruses of the betaherpesvirinae sub-family include human cytomegalovirus, human herpes simplex virus type 6 and human herpes simplex virus type 7. Examples of viruses of the gammaherpesvirinae sub-family include infections of Epstein-Barr virus and Karposi sarcoma herpesvirus.

In one embodiment, the composition is suitable for inhibiting infections by herpes simplex viruses (e.g. herpes simplex virus type 1 and 2), varicella zoster virus and Epstein Barr virus.

The extract is any extract, semi-purified fraction or purified fraction derived from all or part of a plant in the Asteraceae family that is capable of inhibiting herpesviridae infection. For example, the extract may be produced from one or more of the stem, leaves and flowers of a plant.

The extract may be produced by a suitable method, so long as the method of producing the extract does not interfere with the ability of the extract to inhibit infection. In this regard, a suitable extract may be identified by the determination of the ability of an extract to inhibit a herpesviridae infection in vitro and/or in vivo, for example as described in the Examples.

Typically, a single daisy plant is obtained and the stem, leaves and flowers macerated at room temperature in a suitable volume of water (e.g. 20 ml to 250 ml) to produce a water soluble extract.

In one embodiment, the extract is produced by macerating, grinding or crushing all or part of a plant in the Asteraceae family in the presence of a substantially aqueous solvent (e.g. water), to produce a substantially aqueous extract. Examples of plants in the Asteraceae family are as previously discussed.

Accordingly, in another embodiment the present invention provides a method of producing a composition for inhibiting a herpesviridae infection in a subject and/or providing relief from a herpesviridae infection in a subject, the method including extracting all or part of a plant in the Asteraceae family with a substantially aqueous solvent, wherein the plant is not a plant in the sub-families Heliantheae and Asteroideae, or a plant from the genus *Youngia*.

The extract may be further treated to concentrate or partition the active ingredients in the extract by a suitable method known in the art.

In one embodiment, the extract produced from all or part of the plant in water is further extracted with an organic solvent. In this case, the aqueous fraction produced after extraction retains anti-herpesviridae activity.

For example, the aqueous fraction produced may be further extracted with a n-pentane/diethylether mixture to produce an aqueous phase with anti-herpesviridae activity.

An alternative methodology for concentrating the active ingredients is by extracting the material with dichloromethane. The aqueous phase may then be recovered and the solution exposed to a cation exchange resin. After washing the resin and elution with ammonia, a fraction may be collected with anti-herpesviridae activity.

The amount of plant extract is not particularly limited, so long as it is such an amount and in such a form that inhibits the herpesviridae infection.

In this regard, the amount of the plant extract may be appropriately chosen, depending upon the type and extent of infection to be inhibited, and the presence of other active agents.

The present invention may also used to inhibit a herpesviridae infection in a subject, and/or provide relief from a herpesviridae infection in a subject.

Accordingly, in another embodiment the present invention provides a method of inhibiting a herpesviridae infection and/or providing relief from a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

The present invention may also be used in the preparation of a medicament for inhibiting a herpesviridae infection and/or providing relief from a herpesviridae infection in a subject.

Accordingly, in another embodiment the present invention provides use of an effective amount of an extract from a plant in the Asteraceae family in the preparation of a medicament for inhibiting a herpesviridae infection and/or providing relief from a herpesviridae infection in a subject, wherein the extract is not an extract from a plant in the sub-families Heliantheae and Asteroideae, or an extract from a plant in the genus *Youngia*.

The present invention may also be used to treat a herpesviridae infection in a subject.

The present invention may also be used prophylactically, so as to prevent a herpesviridae infection in a subject.

Accordingly, in another embodiment the present invention provides a method of preventing, treating and/or providing relief from a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

The present invention also provides a pharmaceutical composition used for one or more of preventing, treating and providing relief from a herpesviridae infection in a subject.

Accordingly, in another embodiment the present invention provides a pharmaceutical composition when used for one or more of preventing, treating and providing relief from a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides use of the extract in the preparation of a medicament for one or more of preventing, treating and providing relief from a herpesviridae infection in a subject.

Accordingly, in another embodiment the present invention provides use of an effective amount of an extract from a plant in the Asteraceae family in the preparation of a medicament for one or more of preventing, treating and providing relief from a herpesviridae infection in a subject, wherein the extract is not an extract from a plant in the sub-families Heliantheae and Asteroideae, or an extract from a plant in the genus *Youngia*.

The present invention may also be used to prevent and/or treat a disease or condition associated with herpesviridae infection, and/or to provide relief from a disease or condition associated with a herpesviridae infection.

Examples of diseases or conditions associated with viruses of the herpesviridae include chicken pox (varicella-zoster virus), shingles (varicella-zoster virus), herpetic oral ulceration (usually due to herpes simplex virus type 1, but may also be due to herpes simplex type 2), conjunctivitis (herpes simplex virus), genital herpes (usually due to herpes simplex virus type 2, but may also be due to herpes simplex type 1), gingivostomatitis (herpes simplex virus type 1), herpes labialis (herpes simplex virus type 1), neonatal herpes (herpes simplex virus type 2), keratoconjunctivitis (herpes simplex virus type 1), aseptic meninginitis (herpes simplex virus type 2), mononucleosis (Epstein-Barr virus), oral hairy leukoplakia (Epstein-Barr virus), mononucleosis-like syndrome (cytomegalovirus), pharyngitis (Epstein-Barr virus), and viral pneumonia (cytomegalovirus).

Accordingly, in another embodiment the present invention provides a method of preventing, treating and/or providing relief of a disease or condition associated with a herpesviridae infection in a subject, the method including administering to the subject an effective amount of an extract from a plant in the Asteraceae family, wherein the extract is not an extract from a plant in the sub-families Heliantheae and Asteroideae, or an extract from a plant in the genus *Youngia*.

In one embodiment, the present invention provides a method of preventing, treating and/or providing relief of a disease or condition from a disease or condition selected from chicken pox, shingles, herpetic oral ulceration, conjunctivitis, genital herpes, gingivostomatitis, herpes labialis, neonatal herpes, keratoconjunctivitis, aseptic meninginitis, mononucleosis, oral hairy leukoplakia, mononucleosis-like syndrome, pharyngitis, and viral pneumonia, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides a pharmaceutical composition used for one or more of preventing, treating and providing relief of a disease or condition associated with a herpesviridae infection.

Accordingly, in another embodiment the present invention provides a pharmaceutical composition when used for one or more of preventing, treating and providing relief of a disease or condition associated with a herpesviridae infection in a subject, the composition including an effective amount of an extract from a plant in the Asteraceae family, wherein the extract is not an extract from a plant in the sub-families Heliantheae and Asteroideae, or an extract from a plant in the genus *Youngia*.

In one embodiment, the present invention provides a pharmaceutical composition when used for one or more of preventing, treating and providing relief from a disease or condition selected from chicken pox, shingles, herpetic oral ulceration, conjunctivitis, genital herpes, gingivostomatitis, herpes labialis, neonatal herpes, keratoconjunctivitis, aseptic meninginitis, mononucleosis, oral hairy leukoplakia, mononucleosis-like syndrome, pharyngitis, and viral pneumonia, the composition including an effective amount of an extract from a plant in the Asteraceae family, wherein the extract is not an extract from a plant in the sub-families Heliantheae and Asteroideae, or an extract from a plant in the genus *Youngia*.

The present invention also provides use of the extract in the preparation of a medicament for one or more of preventing, treating and providing relief of a disease or condition associated with a herpesviridae infection.

Accordingly, in another embodiment the present invention provides use of an effective amount of an extract from a plant in the Asteraceae family in the preparation of a medicament for one or more of preventing, treating and providing relief of a disease or condition associated with a herpesviridae infection in a subject, wherein the extract is not an extract from a plant in the sub-families Heliantheae and Asteroideae, or an extract from a plant in the genus *Youngia*.

In one embodiment, the present invention provides use of an effective amount of an extract from a plant in the Asteraceae family in the preparation of a medicament for one or more of preventing, treating and providing relief of a disease or condition selected from chicken pox, shingles, herpetic oral ulceration, conjunctivitis, genital herpes, gingivostomatitis, herpes labialis, neonatal herpes, keratoconjunctivitis, aseptic meninginitis, mononucleosis, oral hairy leukoplakia, mononucleosis-like syndrome, pharyngitis, and viral pneumonia, wherein the extract is not an extract from a plant in the sub-families Heliantheae and Asteroideae, or an extract from a plant in the genus *Youngia*.

Inhibition of herpesviridae infection in a human or other suitable animal subject may be determined by a suitable method known in the art.

For example, the extent of inhibition may be determined by the time taken for resolution of the infection in the subject and/or a reduction in the severity of the infection in the subject. Alternatively, an immunological detection method such as ELISA can be used to assess the inhibition of infection.

As will be appreciated, the composition of the present invention will be delivered in a form, and to a site, that is appropriate for the herpesviridae infection to be inhibited.

For example, the composition may be delivered as a topical formulation, a formulation for intravenous delivery, a formulation for delivery as an intramuscular injection, subcutaneous injection or injection into an organ, as a transmucosal preparation for delivery through nasal cavity, rectum, uterus, vagina, lung, etc., or as a formulation for oral administration.

In one embodiment, the pharmaceutical composition is a topical acomposition for inhibiting and/or providing relief from a herpesviridae infection in a human subject.

In a further embodiment, the extract is from all or part of a plant selected from the group consisting of *Chrysanthemum* spp., including *Chrysanthemum frutescens*, varieties referred to as "Marguerite daisy", Ox-eye daisy (*Chrysanthemum leucanthemum*), *Chrysanthemum×morifolium*, *Chrysanthemum parthenium*, *Chrysanthemum vulgare*, *Chrysanthemum anethifolium*, *Chrysanthemum indicum*, and *Chrysanthemum balsamita*; *Olearia* spp., including *Olearia phlogopappa Olearia microphylla, Olearia ramulosa*; *Brachycome* spp., including *Brachycome multida* and *Brachycome iberidfolia*; *Arctotis hybrids*; *Celmisa* spp. including *Celmisa incana*; *Dimorphotheca* spp. including *Dimorphotheca aurantiaca*; and a daisy referred to as white oxyeye, white daisy, paris daisy, dog daisy, goldens, moondaisy, maudlin daisy, field daisy, dun daisy, butter daisy, horse daisy, China aster, *bellis perennis, Leucanthemum vulgare*, or *Argyranthemum frutescens*.

The preparation of pharmaceutical compositions is known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

The composition may also include use of one or more pharmaceutically or therapeutically acceptable additives, including pharmaceutically acceptable salts, amino acids, polypeptides, polymers, solvents, buffers, excipients and bulking agents, all known in the art.

For topical administration, the composition may be, for example, in the form of a solution, spray, lotion, cream (for example a non-ionic cream), gel, paste or ointment. Alternatively, the composition may be delivered via a liposome, nanosome, or nutri-diffuser vehicle. The actual form of the composition will depend upon the particular herpesviridae infection being treated.

A solution for topical delivery may include the plant extract (or a fraction thereof) alone, or may be used in combination with one or more other topically acceptable additives known in the art.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are generally mono-, di- and triglycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste usually contains a large proportion (20-50%) of dispersed solids in a fatty or aqueous vehicle. An ointment tends not to evaporate or be absorbed when rubbed onto the skin.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension, semisolid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, aluminum or zinc soaps.

In the case of a composition for topical administration, the composition may further include one or more drying agents, anti-foaming agents; buffers, neutralizing agents, agents to adjust pH; colouring agents and decolouring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

In the case where the composition is delivered as a spray, the composition for administration will include the plant extract (or a fraction thereof) and may further include one or more suitable additives known in the art. In the case of a spray delivered by atomisation, the composition will not need to include a propellant.

In the case where the composition is used for the inhibition of herpetic gingivostomatitis, herpes labialis, herpetic oral ulceration, genital herpes, and herpes zoster, a suitable administration route is by way of topical administration.

Suitable topical compositions are as follows:

(i) Cream Formulation

An extract from *Chysanthemun frutescens* may be prepared by macerating all or part of the plant in water and 10 ml of the extract so produced combined with 100 grams of a cream containing 15% (v/v) cetomacrogol emulsifying wax, 10% liquid paraffin (w/v), 10% white soft paraffin (v/v), 0.1% (w/v) chlorocresol or a similar antimicrobial or preservative agent, 5% propylene glycol (v/v), in an aqueous base.

(ii) Spray Formulation

An extract from *Chysanthemun frutescens* may be prepared by macerating all or part of the plant in water and 10 ml of the extract so produced combined with water to a total volume of 100 ml. Alternatively, the spray formulation may be formulated as 10% (v/v) plant extract, 0.5% sodium chloride (w/v), 5% propylene glycol (v/v) in an aqueous base.

(iii) Gel Formulation

An extract from *Chysanthemun frutescens* may be prepared by macerating all or part of the plant in water and 10 ml of the extract so produced combined with 100 ml of a gel formulation containing 25% (v/v) gelatin, 40% glycerol (v/v) in an aqueous base. An alternative gel formulation may be prepared as follows: 10 ml of plant extract was combined with 100 ml of a gel formulation containing 0.5% (w/v) sodium chloride, 5% (v/v) propylene glycol in an aqueous base.

In the case where the composition is administered in the form of oral preparations, the composition may be in form of solid preparations such as tablets, capsules, granules or powders; liquid preparations such as syrup, emulsions or suspensions. Compositions containing the extract may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, α-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

If administered orally, the composition may be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the extract optionally with one or more accessory ingredients. Compressed tablets may be prepared by compressing, in a suitable machine, the extract in a free-flowing form such as a powder or granules, optionally mixed with a binder, lubricant, inert diluent, surface active, or dispersing agent. Moulded tablets may be made by molding in a suitable machine, a mixture of the powdered active ingredient and a suitable carrier moistened with an inert liquid diluent.

Pharmaceutical compositions including the plant extract may utilize controlled release or sustained release technology. To further increase the sustained release effect, the composition may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the plant extract may be incorporated into a hydrophobic polymer matrix for controlled release over a period of days. The composition of the invention may then be molded into a solid implant, or externally applied patch, suitable for providing efficacious concentrations of the extract over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers that may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time-release characteristics and release kinetics. The composition may then be moulded into a solid implant suitable for providing efficacious concentrations of the plant extract over a prolonged period of time without the need for frequent re-dosing. The plant extract can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

In the case where the composition is delivered as an injectable, the composition may be administered in a pharmaceutically acceptable form known in the art, for example with normal saline as a vehicle.

DESCRIPTION OF SPECIFIC EMBODIMENTS

Reference will now be made to experiments that embody the above general principles of the present invention. However, it is to be understood that the following description is not to limit the generality of the above description.

Example 1

Production of Plant Extract

An amount of marguerite daisy (*Chysanthemun frutescens*) was macerated in water in a macerator. All or part of the daisy plant was macerated. Typically, a single daisy plant was obtained and the stem, leaves and flowers macerated in water to produce a water soluble extract.

The extract may be used filtered or not-filtered.

Example 2

Formulations Containing Plant Extract (i) Cream Formulation

The extract produced from Example 1 was prepared as a non-ionic cream formulation for topical application as follows:

10 ml of plant extract was combined with 100 grams of a cream containing 15% (v/v) cetomacrogol emulsifying wax, 10% liquid paraffin (w/v), 10% white soft paraffin (v/v), 0.1% (w/v) chlorocresol, 5% propylene glycol (v/v), in an aqueous base.

(ii) Spray Formulation

The extract produced from Example 1 was prepared in a spray formulation for application to the mucosal surfaces of the nose or throat as follows:

10 ml of plant extract was combined with water to a total volume of 100 ml. The spray was then delivered by way of atomization. Alternatively, the spray formulation was formulated as 10% (v/v) plant extract, 0.5% sodium chloride (w/v), 5% propylene glycol (v/v) in an aqueous base.

(iii) Gel Formulation

The extract produced from Example 1 was prepared as a gel formulation for topical application as follows:

10 ml of plant extract was combined with 100 ml of a gel formulation containing 25% (v/v) gelatin, 40% glycerol (v/v) in an aqueous base.

An alternative gel formulation may be prepared as follows: 10 ml of plant extract combined with 100 ml of a gel formulation containing 0.5% (w/v) sodium chloride, 5% (v/v) propylene glycol in an aqueous base.

Example 3

Treatment of Primary Herpetic Gingivostomatitis with Plant Extract

Case 1:

A 16 year old otherwise healthy male presented with a two day history of a febrile illness associated with lip blistering and oral ulceration. There was no history of a herpetic infection. The subject had treated his temperature with paracetamol, which had reduced the temperature from 39.7° C. to 37.9° C. He had been unable to eat for two days due to the severity of the pain.

On examination, a 3.5 cm area of blistering and erythema was present on the skin of the upper lip and on the vermillion of the lower lip. Intraorally, blisters were present on the floor of the mouth and the tonsillar regions of the soft palate.

The clinical findings were those of a primary herpetic gingivostomatitis. The expected time period for resolution of the symptoms of primary herpetic gingivostomatitis without treatment would be expected to be in the range from 10 to 28 days (Fitzpatrick T. B., et al. (1992) in "Colour atlas and synopsis of Clinical Dermatology" McGraw Inc. N.Y.).

The subject consented to be treated with the plant extract in a cream formulation. Upon treatment, the subject reported immediate pain relief. The pain relief was not by way of an anaesthetic or numbing effect.

The extract was applied 5 times a day with administration of paracetamol until the temperature normalised. The subject reported immediate pain relief when the cream was applied to the circum-oral blisters.

The subject was reviewed by telephone 12 hours later and reported a dramatic improvement and was now able to take foods. The subject also reported that the analgesic properties of the plant extract lasted 90 to 120 minutes and that pain relief was evident as soon as the extract was applied.

The subject was reviewed 24 hours later and reported a continued improvement in the size of the lesions and in the oral pain. The lip blister had reduced to 1 cm and the throat ulcers had almost disappeared. The tongue lesions were slower to respond as the subject had difficulty applying the extract.

The subject was reviewed at day 4 and reported a complete resolution 24 hours earlier. Clinically, some mild erythema was noted on the upper lip and no oral or throat lesions were present.

No adverse or hypersensitivity reactions were reported.

Case 2:

A 62 year old female presented with a seven day history of oral ulceration affecting the floor of the mouth. There was no history of prior herpetic infections. The subject reported an associated febrile illness and was unable to eat properly.

On examination, multiple areas of ulceration were present on the floor of the mouth and the ventrum of the tongue.

The clinical findings were those of a primary herpetic gingivostomatitis. The expected time period for resolution of the symptoms of primary herpetic gingivostomatitis is 10 to 14 days.

The subject consented to be treated with the plant extract. The plant extract was delivered in a cream formulation. Upon treatment, the subject reported immediate pain relief. The pain relief was not by way of an anaesthetic or numbing effect.

The extract was applied 5 times a day with administration of paracetamol until the temperature normalised.

At review 48 hours later the subject reported a 40% improvement in the appearance of the lesions and a 75-80% improvement in her symptoms.

The subject ceased treatment with the extract at the end of day 4 as she was asymptomatic and free of lesions. In the early stages, she reported that the analgesia lasted for 30 to 60 minutes and thus increased the frequency of application. After the first 24 hours the analgesia lasted 90 to 120 mins.

No adverse or hypersensitive reactions were reported.

Case 3:

A 31 year old female presented with a thirty hour history of an inability to eat and increasing swelling and burning of the upper lip, gingivae and anterior hard palate. She required paracetamol for pain relief. There was no history of herpetic infections.

On examination, extensive blisters and erythema were present on the right upper lip and erythema of the adjacent ginigivae and the anterior hard palate.

The clinical findings were those of a primary herpetic gingivostomatitis. The subject consented to be treated with the plant extract. The plant extract was delivered in a cream formulation. Upon treatment, the subject reported immediate pain relief. The pain relief was not by way of an anaesthetic or numbing effect.

The extract was applied 5 times a day.

At review by telephone 24 hours later, the subject reported that she was able to eat that morning (13 hours after the initial presentation) and was asymptomatic at 24 hours. No analgesics were required by the subject. The subject reported some tingling of the lip the following day and so recommenced the application of the extract and the tingling ceased after 3 applications (duration of episode 5 to 6 hours).

No adverse or hypersensitive reactions were reported.

A summary of the results is shown in Table 1.

TABLE 1

Summary of treatment of herpetic gingivostomatitis with plant extract

| Age(yrs)/ Sex | Duration of Symptoms | Febrile | Relief of Pain | Time to Complete Healing |
|---|---|---|---|---|
| 16 Male | 2 days | yes | 90-120 mins | 3 days |
| 62 Female | 7 days | yes | 30-60 mins increasing to 90-120 mins after first day | 4 days |
| 31 Female | 30 hours | no | 120 mins | 1 day |

As can be seen, based on this sample of subjects, the mean healing time was 2.7 days. This is significantly faster than the expected 10-28 days if the subjects were treated symptomatically or with acyclovir.

The subjects also reported significant pain management and amelioration of undesired sensations with the plant extract and were able to cease use of paracetamol once their temperature had normalised. No adverse or hypersensitivity reactions were reported.

Example 4

Treatment of Recurrent Herpes Labialis with Plant Extract

An open prospective trial was used to assess the efficacy of the plant extract in the treatment of recurrent herpes labialis. Eight otherwise healthy subjects suffering 37 episodes of the infection entered the study and were treated with the extract in a non-ionic cream that was applied to the lesions 5 times a day. The subjects were reviewed by telephone and in person at regular intervals. The extract was applied by the clinician at the initial examination and any adverse reaction noted.

Case 1:

A 65 year old male with controlled hypertension presented with a four day history of a cold sore on the lip that was stinging and burning. He had a history of recurrent herpes labialis that would normally heal in 7 to 10 days.

The subject consented to be treated with the plant extract in a cream formulation. Upon treatment, the subject reported immediate pain relief. The pain relief was not by way of an anaesthetic or numbing effect.

The cream was applied 5 times a day.

At review by telephone 24 hours later, the subject reported that the lesion had resolved after 12 hours of treatment.

No adverse or hypersensitive reactions were reported.

Case 2:

A 24 year old female presented with a 24 hour history of a stinging and burning sensation at the base of the nostril due to a current herpes labialis infection. The subject had a history of recurrent herpes labialis.

The subject consented to be treated with the plant extract in a cream formulation. Upon treatment, the subject reported immediate pain relief. The pain relief was not by way of an anaesthetic or numbing effect.

The cream was applied 5 times a day and the lesion resolved in 36 hours.

No adverse or hypersensitive reactions were reported.

Case 3:

A 20 year old female presented with a recurrent herpetic lesions on the lip that would usually take 7 days to resolve. The current blisters started 24 hours earlier after 2 hours of tingling. The lesions were sensitive and burning.

The subject consented to be treated with the plant extract in a cream formulation. Upon treatment, the subject reported immediate pain relief. The pain relief was not by way of an anaesthetic or numbing effect.

The cream was applied 5 times a day and the subject reported complete resolution of the lesion by 24 hours.

No adverse or hypersensitive reactions were reported.

Case 4:

A 28 year old female presented with a history of recurrent herpetic lip lesions. The lesions would usually heal in 7-10 days. The current lesion developed 36 hours and was stinging and burning.

The subject consented to be treated with the plant extract in a cream formulation. Upon treatment, the extract eased the discomfort so that "it felt normal".

The cream was applied 5 times a day and the subject reported complete resolution of the lesion in 24 hours.

No adverse or hypersensitive reactions were reported.

Case 5:

A 30 year old female with a history of cold sores that would usually resolve in 7 to 10 days presented with a herpetic lesions that started 24 hours earlier and was localized to the lower left lip. The lesion was burning and was extremely sensitive when eating.

The subject consented to be treated with the plant extract in a cream formulation. Upon treatment, the subject reported immediate pain relief. The pain relief was not by way of an anaesthetic or numbing effect.

The cream was applied 5 times a day. At review by telephone 24 hours later, she reported to be at least 70% better. The lesion resolved within 36 hours.

No adverse or hypersensitive reactions were reported.

Case 6:

A 40 year old female presented with a history of recurrent cold sores occurring twice a year and lasting 7 days. At presentation, she reported mild to moderate discomfort from her lip lesion that had been present for 24 hours.

The subject consented to be treated with the plant extract. Upon treatment, the lesion was 60-70% better at 24 hours and had resolved completely by 30 hours.

No adverse or hypersensitive reactions were reported.

Case 7:

A 50 year old healthy male presented with a 48 hour history of a cold sore on the lower lip. Such lesions would usually resolve within 10 days. The subject reported that the area was tender and sore.

The subject consented to be treated with the plant extract. Upon treatment, the subject reported that the extract immediately eased his symptoms so that it felt "normal".

The cream was applied 5 times a day. At review 24 hours later, the subject reported that he was 50% better and the lesion had resolved completely in 36 hours.

No adverse or hypersensitive reactions were reported.

Case 8:

A 25 year old healthy female presented with a long history of recurrent herpes labialis that would last 7 to 10 days. Over the last three years, the subject had used the extract on 30 episodes of recurrent infection. On each occasion, the tingling and burning was immediately eased by the application of the extract.

The subject reported that if the lesion was treated as soon as it developed (i.e. within the first 24 hours), the lesion would resolve within 24 hours, but if there was a delay, it would last 36 to 48 hours.

No adverse or hypersensitive reactions were reported.

A summary of the results is shown in Table 2.

TABLE 2

Summary of results of treatment of herpes labialis with plant extract

| Age(yrs)/Sex | Duration of Lesion | Relief of Pain | Time to Complete Healing |
| --- | --- | --- | --- |
| 65 Male | 4 days | immediate | 12 hours |
| 20 Female | 1 day | immediate | 24 hours |
| 24 Female | 1 day | immediate | 36 hours |
| 28 Female | 1.5 days | immediate | 12 hours |
| 30 Female | 1 day | immediate | 36 hours |
| 40 Female | 1 day | immediate | 30 hours |
| 50 Male | 2 days | immediate | 36 hours |
| 25 Female | 12 lesions @ 0.5 days | immediate | 12 hours |
|  | 16 lesions @ 1 day | immediate | 24 hours |
|  | 2 lesions @ 1.5 days | immediate | 36 hours |

Seven subjects each suffered 1 episode of recurrent herpes labialis and the eighth suffered 30 episodes.

In each case the subjects reported immediate relief of pain on application of the extract. The mean duration of the herpetic lesion prior to treatment was 24 hours. No adverse or hypersensitivity reactions were reported. The mean time for complete healing was 21 hours.

Studies with acyclovir have stressed the importance of early treatment. Rabon et al. (1989) Oral Surg., Oral Med., Oral Path. 67:676-679 have reported that treatment commenced within 1 hour and achieved analgesia within 1-2 days. Complete healing under these conditions occurred in 7-8 days.

Thus the agent facilitated the resolution of herpes labialis lesions in 14% of the time for acyclovir, in a modified aqueous base, and in lesions that had been present for 24 hours and longer.

Example 5

Treatment of Recurrent Herpetic Oral Ulceration

The lesions associated with recurrent herpetic oral ulceration (stomatitis) commonly affect the attached gingivae, palate, tongue and buccal mucosa. Prodromal symptoms are rarely reported and the vesicles break soon after forming due to the frictional forces in the mouth. As such, the lesions are extremely painful and limit the ability of the subject to eat. The lesions usually heal in 7-10 days without scarring (Shafer W. G. et al. (1983) in "A textbook of oral pathology" WE Saunders. (Phil)).

An open prospective trial was used to assess the efficacy of the extract in the treatment of recurrent herpetic oral ulceration. Nine otherwise healthy subjects entered the study and were treated with the extract in a non-ionic cream that was applied to the lesions 5 times a day. Eight subjects had single episodes and the ninth subject had 2 episodes of herpetic ulceration. The subjects were reviewed by telephone and in person at regular intervals. The agent was applied by the clinician at the initial consultation and any adverse reactions were noted.

Case 1:
A 32 year old female presented with a 2 day history of pain on the tip of the tongue that had prevented her from eating. She reported a history of cold sores that would usually heal in 7-10 days. The clinical findings were those of herpetic ulceration.

The extract was applied and afforded her immediate relief. It was applied 5 times a day and at review by telephone 24 hours later, she reported a 70-80% improvement and she was now able to eat properly. At review, she reported that the lesions had completely resolved within 36 hours.

No adverse or hypersensitivity reactions were reported
Case 2:
An otherwise healthy 27 year old female presented in acute distress due to a 5 hour history of palatal ulceration. She reported a history of cold sores. The palatal ulcers affected the mucosa covering an exostosis. The clinical findings were those of herpetic ulceration.

The extract was applied and afforded her immediate relief. It was prescribed 5 times a day and the lesion resolved in 36 hours.

No adverse or hypersensitivity reactions were reported.
Case 3:
A healthy 18 year old female presented in acute distress due to her oral ulceration on the hard palate that had been present for 30 hours. She had been unable to eat due to the discomfort. She reported a history of herpes labialis in association with sunburn. The clinical findings were those of herpetic ulceration.

The extract was applied and afforded her immediate relief. The extract was prescribed 5 times a day and the lesions resolved over the following 48 hours.

No adverse or hypersensitivity reactions were reported.
Case 4:
A healthy 18 year old female with a history of herpes labialis presented with a 1 day history of ulceration on the tongue and adjacent lower lip. She reported a mild discomfort in the region, but felt that the symptoms were intensifying. The clinical findings were those of herpetic ulceration.

The agent was applied and afforded her immediate relief. It was prescribed 5 times a day and the lesions had resolved in 24 hours.

No adverse or hypersensitivity reactions were reported.
Case 5:
An 18 year old female presented in acute discomfort due to a 24 hour history of palatal ulceration behind the maxillary incisor teeth. She had been unable to eat in this region. She reported a history of cold sores that usually resolved in 10-12 days. The clinical findings were those of herpetic ulceration.

The extract was applied and afforded her immediate relief and she was able to eat more comfortably. The extract was applied 5 times a day and the lesions resolved completely in 36 hours.

No adverse or hypersensitivity reactions were reported.
Case 6:
A healthy 28 year old female with a history of recurrent herpetic lesions presented with a 1 day history of acute discomfort due to ulcers in her plate and adjacent buccal mucosa. She had been unable to eat due to the discomfort. The clinical findings were those of herpetic ulceration.

The extract was applied and afforded her immediate relief. Symptomatic relief was maintained provided the extract was reapplied 5 times a day as had been prescribed. She was able to normalize her diet and the lesions resolved in 36 hours.

No adverse or hypersensitivity reactions were reported.
Case 7:
A healthy 30 year old lady presented with a 10 hour history of pain on the hard palate and an inability to eat. She reported a history of cold sores that would resolve in 7-10 days. Clinically, an area of ulceration was present on the palatal vault. These findings were those of herpetic ulceration.

The extract was applied and afforded her immediate relief. The extract was applied 5 times a day and she reported to be free of pain provided the extract was used. The lesion resolved in 24 hours.

No adverse or hypersensitivity reactions were reported.
Case 8:
A 35 year old healthy female presented with a 5 hour history of painful upper and lower gums which prevented her from eating. She required panadeine for pain relief. She reported a history of herpetic infection. The clinical findings were those of a recurrent herpetic ulceration.

The agent was applied and afforded her immediate analgesia. The agent was applied 5 times a day and she reported to be 60% better at 24 hours. The lesions had completely resolved by 36 hours.

No adverse or hypersensitivity reactions were reported.
Case 9:
A 54 year old female who takes hormone replacement therapy reported a history of recurrent herpetic ulceration that could affect the palate and adjacent cheek mucosa. The lesions were extremely painful and would take at least 10 days to resolve. At presentation, she reported a 3 day history of pain and stinging in the right cheek mucosa.

On examination a herpetic ulcer was present on the right cheek mucosa and the anterior hard palate.

The agent was applied and afforded her immediate relief that lasted for 90 mins. She was reviewed by telephone 24 hours later and reported to be 80% better and the symptoms were controlled by the applications 5 times a day. She later reported that she was completely free of lesions and symptoms within 16 hours.

While on holidays, 2 months later she developed identical lesions (herpetic) that were present for 12 hours prior to the commencement of the agent.

The agent was applied and pain relief was immediate. The lesions resolved in 36 hours.

There were no adverse or hypersensitivity reactions.

A summary of the results is shown in Table 3.

TABLE 3

Summary of results of treatment of oral herpetic ulceration with plant extract

| Age(yrs)/Sex | Duration of Symptoms | Pain Relief | Time to Complete Healing |
|---|---|---|---|
| 32 Male | 48 hours | immediate | 36 hours |
| 27 Female | 5 hours | immediate | 36 hours |
| 18 Female | 30 hours | immediate | 48 hours |
| 18 Female | 24 hours | immediate | 24 hours |
| 18 Female | 24 hours | immediate | 36 hours |
| 28 Female | 24 hours | immediate | 36 hours |
| 30 Female | 10 hours | immediate | 24 hours |
| 35 Female | 5 hours | immediate | 36 hours |
| 54 Female | 72 hours | immediate | 36 hours |
|  | 12 hours | immediate | 36 hours |

In each instance, the subjects reported immediate pain relief with the use of the extract. Treatment with the extract allowed them to improve their dietary intake.

The mean duration of symptoms prior to treatment was 25.4 hours and the mean duration of healing was 34.8 hours. No adverse or hypersensitivity reactions were reported.

The usual treatment for oral herpetic ulceration is a palliative local anaesthetic mouthwash. The lesions would usually heal in 7-10 days Thus treatment with the extract results in healing of recurrent herpetic oral ulceration in 15-21% of the time that would normally be expected.

Example 6

Treatment of Herpetic Genital Infection

An open prospective trial was used to assess the efficacy of the agent in the treatment of recurrent genital herpetic infection. Two otherwise healthy subjects entered the study and were treated with the agent in a non-ionic cream that was applied 5 times a day. It was applied as soon as the lesion appeared.

Case 1:

A 35 year old female presented with a long history of recurrent genital herpetic infection that had in the past required prolonged courses of systemic acyclovir. Within 2 days of ceasing the medication, new lesions would develop.

The subject was prescribed the extract and was told to apply it 5 times a day as required. The subject reported that there was a significant decrease in both the duration and the frequency of the lesions while the agent was used. The results of treatment are shown in Table 4.

TABLE 4

Results of treatment of genital herpes with plant extract

| Date of Onset | Time for lesions to resolve (days) | Interval between attacks (days) |
|---|---|---|
| Nov. 7, 1993 | 1 | — |
| Nov. 24, 1993 | 2 | 16 |
| Jan. 11, 1994 | 2 | 46 |
| Jan. 15, 1994 | 2 | 2 |
| Feb. 3, 1994 | 1 | 17 |

No adverse or hypersensitivity reactions were reported.

Case 2:

A 40 year old female had a long history of recurrent genital herpetic infection that required prolonged courses of systemic acyclovir. Within 7 days of the cessation of the lesions, new lesions would develop.

The subject was prescribed the extract and told to apply it 5 times a day as required. The subject reported that there was a significant decrease in the frequency and the duration of the lesions while the agent was used. The results are shown in Table 5.

TABLE 5

Results of treatment of genital herpes with plant extract

| Date of Onset | Time for lesions to resolve (days) | Interval between attacks (days) |
|---|---|---|
| Jan. 30, 1993 | 1 | — |
| Feb. 24, 1993 | 1 | 23 |
| Mar. 13, 1994 | 1 | 19 |

No adverse or hypersensitivity reactions were reported.

Summary:

Both female subjects had been on prolonged courses of oral acyclovir and both experienced recurrence of the problem shortly after its cessation. Both subjects reported an increased interval between attacks when treated with the extract. No adverse or hypersensitivity reactions were reported.

There was a total of 8 attacks and the mean duration of healing was 1.3 days. This was significantly shorter than the 7.4 day healing rate observed in subjects treated with topical acyclovir (Corey et al. (1982) N. Engl. J. Med. 306:1313-1319) and the 5 day healing rate seen in subjects treated with oral acyclovir (Nilsen et al. (1982) Lancet ii:571-573).

Thus, when recurrent genital herpetic infection was treated with the extract, the healing time was 18% of that observed with topical acyclovir and 26% of the healing time of that seen with oral acyclovir.

Example 7

Treatment of Herpes Zoster

An open prospective trial was used to assess the efficacy of the extract in the treatment of herpes zoster. Two otherwise healthy subjects were treated with the extract. It was applied hourly for the first 24 hours and then 2 hourly. The clinical details are outlined below.

Case 1:

A 76 year old otherwise healthy male reported developing a transient tingling sensation on the scalp of his right forehead. At day 3 he noted a subtle erythematous localized rash in the right eyebrow. He arrived in Adelaide, South Australia on a holiday later in the week and the extent of the rash had extended.

He attended Flinders Medical Centre (SA) on the morning of day 6 and a diagnosis of herpes zoster was made. With the informed consent of the subject, he was treated with the extract in the form of a gel and it was applied hourly for the first 24 hours and then 5 times a day. The area was not washed until day 9.

At presentation, extensive areas of blistering were present on the right scalp that followed the distribution of the opthalmic division of the trigeminal nerve.

At review 1 hour later, a significant erythema was noted. The subject reported significant and immediate pain relief with each application of the extract. Occasional breakthrough pain occurred towards the end of the day and was controlled by panadeine. No new lesions were observed.

At 2.5 hours post initial application, initial crusting was observed and no new lesions were present.

The subject was reviewed by an ophthalmologist at FMC on 3 occasions as a uveitis developed and was treated with prednisolone drops. No viral ocular involvement occurred.

At review of day 4, the lesions showed evidence of increased healing and no new lesions were seen.

By day 7 the affected area was extremely dry and scaly and for this reason the extract was changed to a cream base and was applied 5 times a day.

At review on day 8, a further and significant improvement was noted. The subject was free of pain. The subject left the country the following day and continued with the extract until he ran out 6 days later.

At day 21 the lesion were almost completely healed.

No adverse or hypersensitivity reactions were reported.

Case 2:

A 93 year old lady with controlled hypertension (Renitec & Minipress) presented with a 7 day history of oral ulceration and blisters on the skin in keeping with herpes zoster affecting the right division of the trigeminal nerve. She was prescribed acyclovir tablets 5 days earlier and required both Digesic 4 hourly and MS Contin (morphine) 30 g 2 times a day for pain relief. The oral lesions were causing her significant distress and she was unable to eat anything but luke warm soup or yoghurt.

On examination, multiple local crusted lesions were present in the right preauricular and lip and chin region of the face. Intraorally extensive areas of ulceration were present on the right dorsum and lateral margin of the tongue.

The subject consented to being treated with the extract that afforded her significant and almost immediate pain relief (within 5 minutes). The relief lasted 60-90 minutes and the discomfort was largely controlled with the extract, applying it at ~60-90 minute intervals for the first 24 hours and then 2 hourly.

At review 24 hours later, the lesions had reduced to such an extent that the LMO ceased the acyclovir and the extract was continued. She reported a need for analgesics at the end of the day and both Digesic and MS Contin were required. This represented a significant reduction in the intake of painkillers. She was also able to improve her dietary intake and was comfortably managing a wider range of foods.

At review on day 4, the viral lesions continued to improve and there was no evidence of rebound on withdrawal of the acyclovir. The subject was now managing a normal diet.

At review on day 5, there was a continued improvement but she still required Ms Contin at the end of the day for pain relief.

At review of day 7, there was a continued improvement, but her pain at the end of the day continued to be a management problem.

All lesions had completely resolved on day 9.

She experiences an ongoing problem of postherpetic neuralgia that was partially responsive to Ms Contin and topical capsaicin.

Summary:

In case 1, relief was achieved by and large with the extract alone and no new lesions developed after the commencement of the extract. Initial crusting was observed after 2.5 hours of treatment as compared with 2-3 days for initial crusting when subjects are treated with acyclovir (Esmann et al. (1982) Am. J. Med. 73(1A):320-325; Bean et al (1983) J. Antimicrob Chemo 12 (Sup B):123-127). The subject recovered far more rapidly than would have been expected if acyclovir was used.

In case 2, the degree of pain was far greater and the use of the agent allowed a significant reduction in the use of both digesic and Ms Contin. While a significant amount of scabbing extraorally had occurred with the use of acyclovir, intraorally ulceration and pain were still a significant problem at the time of commencement of the agent. All lesions responded within 24 hours of the use of the agent.

In conclusion, in both instances, the extract displayed a significant therapeutic benefit to these subjects with herpes zoster. Initial scabbing was observed in case 1 in 4% of the time expected with oral acyclovir.

Example 8

Treatment of Oral Hairy Leukoplakia

Oral hairy leukoplakia (OHL) presents as white corrugated lesions on the lateral and dorsal aspects of the tongue and may extend onto the buccal mucosae. It is thought to be due to an epithelial proliferation due to EBV.

A range of treatment options have been reported. Systemic acyclovir resulted in the resolution of OHL in 12/14 subjects after 20 days (Herbst et al. (1989) JAAD 12:753-756) and Resnick et al (1988) JAMA 259:374-388 reported a response of 5/6 after 10 days of oral acyclovir.

An open prospective trial was used to assess the efficacy of the extract in the treatment of Oral Hairy Leukoplakia. Three subjects entered the study and were prescribed the extract in a non-ionic cream 5 times a day. The clinician applied the extract in the surgery and no adverse reactions were noted. The clinical details are summarized below.

Case 1:

A 70 year old male reported a 6 month history of a roughened and tender lateral margin of his tongue. He was taking Aspirin, Lanoxin, Betaloc, Minipress and Deptran to control his cardiovascular disease and depression. He was otherwise well and was a non-smoker and a non-alcohol consumer.

On examination, corrugated white lesions were present on the lateral margins of the tongue and extended onto the dorsum.

The lesion was biopsied and the histopathology was characteristic of oral hairy leukoplakia, with EBV being demonstrated in the koilocytes (EM and EBV probe). He was HIV negative.

The subject was treated with the extract 5 times a day. At review 3 days later, the lesions had resolved.

No adverse or hypersensitivity reactions were reported

Case 2:

A 45 year old healthy male presented with a 3 week history of focal white patches on the anterior dorsum and lateral margins of the tongue. A biopsy was performed and the histopathology confirmed the clinical diagnosis of oral hairy leukoplakia.

The lesion was treated with the agent 5 times a day and the lesion resolved completely in 4 days.

No adverse or hypersensitivity reactions were reported.

Case 3:

A 36 year old male with cutaneous psoriasis and oral pemphigus vegetans presented. He developed sensitive corrugated white lesions on the lateral margins of his tongue after a course of topical corticosteroids for his oral pemphigus. These findings were those of biopsy proven oral hairy leukoplakia.

He was treated with the extract and the sensitivity and mild discomfort resolved immediately. It was applied 5 times a day and the lesions resolved in 3 days. No adverse or hypersensitivity reactions were reported.

Summary:

The 3 cases treated with the agent responded in a 3.3 day period (mean), which compares with a response time of at least 10-20 days with oral acyclovir (Herbst et al. (1989) JAAD 12:753-756) and Resnick et al (1988) JAMA 259: 374-388).

Thus it was seen that OHL responded within 33% of the expected time with oral acyclovir.

Example 9

Overview of Treatment of Viral Infections with Extract

A summary of the results of the treatment of various viral infections with the plant extract are shown in Table 6.

TABLE 6

Summary of treatment of various viral infections with plant extract

| Diagnosis | Number of cases | Healing Time with plant extract (mean) | Expected healing time Acyclovir |
|---|---|---|---|
| Primary Herpetic Stomatitis | 3 | 2.7 | 10 days to 4 weeks |
| Recurrent Herpes Labialis | 8 (37 episodes) | 21 hours | 7-8 days |
| Recurrent Herpetic Oral Ulceration | 9 (10 episodes) | 34.8 hours | Unknown Normal Healing 7-10 days |
| Recurrent Genital Herpetic Infection | 2 (8 episodes) | 1.3 days | 7.4 days topical 5 days oral |
| Herpes Zoster | 2 | 2.5 hours with initial crusting | 2-3 days initial crusting |

TABLE 6-continued

Summary of treatment of various viral infections with plant extract

| Diagnosis | Number of cases | Healing Time with plant extract (mean) | Expected healing time Acyclovir |
|---|---|---|---|
| Oral Hairy Leukoplakia | 3 | 3.3 days | 10-20 days - oral |

Finally, it will be appreciated that various modifications and variations of the described methods and compositions of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the art are intended to be within the scope of the present invention.

The invention claimed is:

1. A method of treating shingles in a subject in need thereof, said method comprising topically applying to a lesion and/or an area affected with shingles an effective amount of a composition comprising: a water soluble extract of *Chrysanthemum frutescens* obtained by macerating, grinding or crushing all or part of a *Chrysanthemum frutescens* plant in an aqueous solvent to provide the water soluble extract, and a topically acceptable additive.

2. The method according to claim 1, wherein the composition is formulated as a cream, a lotion, a paste, an ointment, a gel or a spray.

3. A method of providing symptomatic relief from shingles in a subject with shingles in need thereof, said method comprising topically applying to a lesion and/or affected area associated with the shingles an effective amount of a composition comprising: a water soluble extract of *Chrysanthemum frutescens* obtained by macerating, grinding or crushing all or part of a *Chrysanthemum frutescens* plant in an aqueous solvent to provide the water soluble extract, and a topically acceptable additive.

4. The method according to claim 3, wherein the composition is formulated as a cream, a lotion, a paste, an ointment a gel or a spray.

5. The method according to claim 3, wherein the relief comprises analgesia without an anaesthetic or numbing effect.

* * * * *